United States Patent
Bouchard et al.

[11] Patent Number: 5,777,139
[45] Date of Patent: Jul. 7, 1998

[54] TAXOIDS, THEIR PREPARATION AND PHARMACEUTICAL COMPOSITIONS CONTAINING THEM

[75] Inventors: Hervé Bouchard, Thiais; Jean-Dominique Bourzat, Vincennes; Alain Commerçon, Vitry-sur-Seine, all of France

[73] Assignee: Rhone-Poulenc Rorer S.A., Antony, France

[21] Appl. No.: 750,090

[22] PCT Filed: Jun. 7, 1995

[86] PCT No.: PCT/FR95/00736

§ 371 Date: Dec. 6, 1996

§ 102(e) Date: Dec. 6, 1996

[87] PCT Pub. No.: WO95/33737

PCT Pub. Date: Dec. 14, 1995

[30] Foreign Application Priority Data

Jun. 9, 1994 [FR] France .................... 94 07050

[51] Int. Cl.$^6$ ............ C07D 305/14; A61K 31/335
[52] U.S. Cl. ............ 549/510; 549/511; 514/449
[58] Field of Search ............ 549/510, 511; 514/449

[56] References Cited

FOREIGN PATENT DOCUMENTS

| | | |
|---|---|---|
| 577082 | 1/1994 | European Pat. Off. . |
| 577083 | 1/1994 | European Pat. Off. . |
| 590267 | 4/1994 | European Pat. Off. . |
| WO-93/06093 | 4/1993 | WIPO . |

*Primary Examiner*—Ba K. Trinh
*Attorney, Agent, or Firm*—Finnegan, Henderson, Farabow, Garrett & Dunner, L.L.P.

[57] ABSTRACT

This invention relates to taxoids of the formula (I):

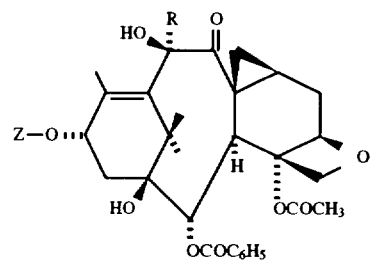

a method for preparing these taxoids, and pharmaceutical compositions containing them. In formula (I), R is alkyl radical (1–6 carbon atoms), alkenyl (2–6 carbon atoms), alkynyl (2–6 carbon atoms), cycloalkyl (3–6 carbon atoms), cycloalkenyl (4–6 carbon atoms), phenyl, unsaturated heterocyclyl containing from 5 to 6 links, Z is a hydrogen atom or a radical of formula (II):

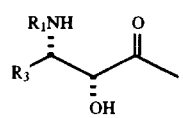

wherein $R_1$ is an optionally substituted benzoyl radical, thenoyl radical, furoyl radical, or a radical $R_2$—O—CO— in which $R_2$ is an alkyl, alkenyl, alkynyl, cycloalkyl, cycloalkenyl, bicycloalkyl, optionally substituted phenyl or heterocyclyl, and $R_3$ is an alkyl, alkenyl, alkynyl, cycloalkyl, phenyl, naphthyl or aromatic heterocyclic radical. The taxoids of formula (I) in which Z is a radical of formula (II) have remarkable antitumoral and antileukemic properties.

16 Claims, No Drawings

TAXOIDS, THEIR PREPARATION AND PHARMACEUTICAL COMPOSITIONS CONTAINING THEM

This is a 371 application of PCT/FR95/00736 dated Jun. 7, 1995, published as WO95/33737, Dec. 14, 1995.

The present invention relates to relates to new taxoids of general formula:

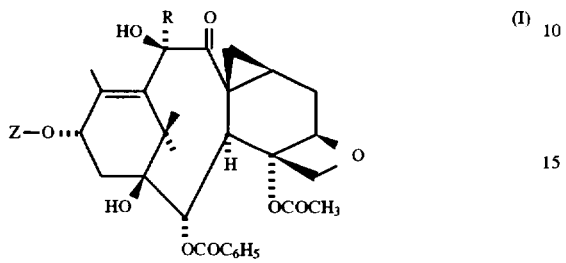

in which:

R represents an unbranched or branched alkyl radical containing 1 to 6 carbon atoms, an unbranched or branched alkenyl radical containing 2 to 6 carbon atoms, an unbranched or branched alkynyl radical containing 2 to 6 carbon atoms, a cycloalkyl radical containing 3 to 6 carbon atoms, a cycloalkenyl radical containing 4 to 6 carbon atoms, an aryl radical or a 5- to 6-membered aromatic heterocyclic radical, Z represents a hydrogen atom or a radical of general formula:

in which:

$R_1$ represents a benzoyl radical optionally substituted with one or more identical or different atoms or radicals chosen from halogen atoms and alkyl radicals containing 1 to 4 carbon atoms, alkoxy radicals containing 1 to 4 carbon atoms or trifluoromethyl radicals, a thenoyl or furoyl radical or a radical $R_2$—O—CO— in which $R_2$ represents:

an alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals being optionally substituted with one or more substituents chosen from halogen atoms and hydroxyl radicals, alkoxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals (optionally substituted with one or more atoms or radicals chosen from halogen atoms and alkyl radicals containing 1 to 4 carbon atoms or alkoxy radicals containing 1 to 4 carbon atoms), cyano or carboxyl radicals or alkoxycarbonyl radicals in which the alkyl portion contains 1 to 4 carbon atoms, a phenyl or α- or β-naphthyl radical optionally substituted with one or more atoms or radicals chosen from halogen atoms and alkyl radicals containing 1 to 4 carbon atoms or alkoxy radicals containing 1 to 4 carbon atoms, or a 5-membered aromatic heterocyclic radical preferably chosen from furyl and thienyl radicals, or a saturated heterocyclic radical containing 4 to 6 carbon atoms, optionally substituted with one or more alkyl radicals containing 1 to 4 carbon atoms, $R_3$ represents an unbranched or branched alkyl radical containing 1 to 8 carbon atoms, an unbranched or branched alkenyl radical containing 2 to 8 carbon atoms, an unbranched or branched alkynyl radical containing 2 to 8 carbon atoms, a cycloalkyl radical containing 3 to 6 carbon atoms, a phenyl or α- or β-naphthyl radical optionally substituted with one or more atoms or radicals chosen from halogen atoms and alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro and trifluoromethyl radicals, or a 5-membered aromatic heterocycle containing one or more identical or different hetero atoms chosen from nitrogen, oxygen and sulphur atoms and optionally substituted with one or more identical or different substituents chosen from halogen atoms and alkyl, aryl, amino, alkylamino, dialkylamino, alkoxycarbonylamino, acyl, arylcarbonyl, cyano, carboxyl, carbamoyl, alkylcarbamoyl, dialkylcarbamoyl or alkoxycarbonyl radicals, on the understanding that, in the substituents of the phenyl, α- or β-naphthyl and aromatic heterocyclic radicals, the alkyl radicals and the alkyl portions of the other radicals contain 1 to 4 carbon atoms, and that the alkenyl and alkynyl radicals contain 2 to 8 carbon atoms, and that the aryl radicals are phenyl or α- or β-naphthyl radicals.

Preferably, the aryl radicals which can be represented by R and $R_3$ are phenyl or α- or β-naphthyl radicals optionally substituted with one or more atoms or radicals chosen from halogen atoms (fluorine, chlorine, bromine, iodine) and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and the alkyl portions of the other radicals contain 1 to 4 carbon atoms, that the alkenyl and alkynyl radicals contain 2 to 8 carbon atoms and that the aryl radicals are phenyl or α- or β-naphthyl radicals.

Preferably, the heterocyclic radicals which can be represented by R and $R_3$ are 5-membered aromatic heterocyclic radicals containing one or more identical or different atoms chosen from nitrogen, oxygen and sulphur atoms, optionally substituted with one or more identical or different substituents chosen from halogen atoms (fluorine, chlorine, bromine, iodine) and alkyl radicals containing 1 to 4 carbon atoms, aryl radicals containing 6 to 10 carbon atoms, alkoxy radicals containing 1 to 4 carbon atoms, aryloxy radicals containing 6 to 10 carbon atoms, amino radicals, alkylamino radicals containing 1 to 4 carbon atoms, dialkylamino radicals in which each alkyl portion contains 1 to 4 carbon atoms, acylamino radicals in which the acyl portion contains 1 to 4 carbon atoms, alkoxycarbonylamino radicals containing 1 to 4 carbon atoms, acyl radicals containing 1 to 4 carbon atoms, arylcarbonyl radicals in which the aryl portion contains 6 to 10 carbon atoms, cyano, carboxyl or carbamoyl radicals, alkylcarbamoyl radicals in which the alkyl portion contains 1 to 4 carbon atoms, dialkylcarbamoyl radicals in which each alkyl portion contains 1 to 4 carbon atoms or alkoxycarbonyl radicals in which the alkoxy portion contains 1 to 4 carbon atoms.

More especially, the present invention relates to the products of general formula (I) in which R represents an alkyl radical containing 1 to 4 carbon atoms, Z represents a hydrogen atom or a radical of general formula (II) in which $R_1$ represents a benzoyl radical or a radical $R_2$—O—CO— in which $R_2$ represents a tert-butyl radical and $R_3$ represents an alkyl radical containing 1 to 6 carbon atoms, an alkenyl radical containing 2 to 6 carbon atoms, a cycloalkyl radical containing 3 to 6 carbon atoms, a phenyl radical optionally substituted with one or more identical or different atoms or radicals chosen from halogen atoms (fluorine, chlorine) and alkyl (methyl), alkoxy (methoxy), dialkylamino (dimethylamino), acylamino (acetylamino), alkoxycarbonylamino (tert-butoxycarbonylamino) or trifluoromethyl radicals, or a 2- or 3-furyl, 2- or 3-thienyl or 2-, 4- or 5-thiazolyl radical.

Still more especially, the present invention relates to the products of general formula (I) in which R represents a methyl radical, Z represents a hydrogen atom or a radical of general formula (II) in which $R_1$ represents a benzoyl radical or a radical $R_2$—O—CO— in which $R_2$ represents a tert-butyl radical and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl or 5-thiazolyl radical.

The products of general formula (I) in which Z represents a radical of general formula (II) display noteworthy antitumour and antileukaemic properties.

According to the present invention, the products of general formula (I) in which R and Z are defined as above may be obtained by the action of an organometallic derivative of general formula:

R—X  (III)

in which R is defined as above and X represents a metal atom such as a lithium atom or an organomagnesium residue (Mg—Y in which Y represents a halogen atom), on a product of general formula:

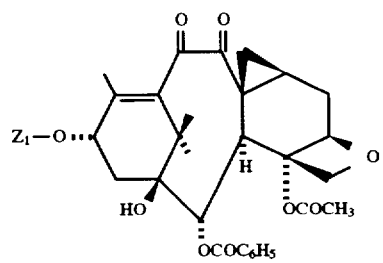

(IV)

in which $Z_1$ represents a hydrogen atom or a radical of general formula:

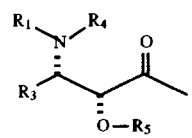

(V)

in which $R_1$ and $R_3$ are defined as above, and either $R_4$ represents a hydrogen atom and $R_5$ represents a group protecting the hydroxyl function, or $R_4$ and $R_5$ together form a heterocycle, to obtain a product of general formula:

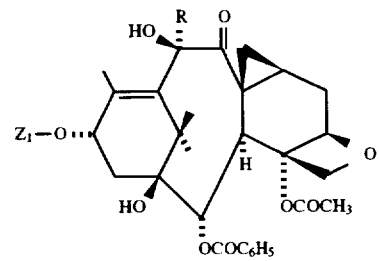

(VI)

followed, where appropriate, by replacement of the protective groups represented by $R_5$ of/or $R_4$ and $R_5$ and the Z moiety by hydrogen atoms.

Generally, the process is carried out in an inert organic solvent such as an ether (tetrahydrofuran) at a temperature of between −78° and 30° C.

Preferably, $R_4$ represents a hydrogen atom and $R_5$ represents a group protecting the hydroxyl function, or alternatively $R_4$ and $R_5$ together form a 5- or 6-membered saturated heterocycle.

When $R_4$ represents a hydrogen atom, $R_5$ preferably represents a methoxymethyl, 1-ethoxyethyl, benzyloxymethyl, trimethylsilyl, triethylsilyl, β-trimethylsilyloxymethyl, benzyloxycarbonyl or tetrahydropyranyl radical.

When $R_4$ and $R_5$ together form a heterocycle, the latter is preferably an oxazolidine ring optionally monosubstituted or gem-disubstituted at position 2.

Replacement of the protective groups $R_5$ and/or $R_4$ and $R_5$ by hydrogen atoms may be performed, depending on their nature, in the following manner:

1) when $R_4$ represents a hydrogen atom and $R_5$ represents a group protecting the hydroxyl function, replacement of the protective groups by hydrogen atoms is performed by means of an inorganic acid (hydrochloric acid, sulphuric acid, hydrofluoric acid) or organic acid (acetic acid, methanesulphonic acid, trifluoromethanesulphonic acid, p-toluenesulphonic acid) used alone or mixed, working in an organic solvent chosen from alcohols, ethers, esters, aliphatic hydrocarbons, halogenated aliphatic hydrocarbons, aromatic hydrocarbons or nitriles at a temperature of between −10° and 60° C., 2) when $R_4$ and $R_5$ together form a 5- or 6-membered saturated heterocycle, and more especially an oxazolidine ring of general formula:

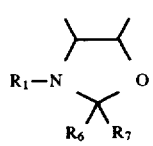

(VII)

in which $R_1$ is defined as above and $R_6$ and $R_7$, which may be identical or different, represent a hydrogen atom or an alkyl radical containing 1 to 4 carbon atoms, or an aralkyl radical in which the alkyl portion contains 1 to 4 carbon atoms and the aryl portion preferably represents a phenyl radical optionally substituted with one or more alkoxy radicals containing 1 to 4 carbon atoms, or an aryl radical preferably representing a phenyl radical optionally substituted with one or more alkoxy radicals containing 1 to 4 carbon atoms, or alternatively $R_6$ represents an alkoxy radical containing 1 to 4 carbon atoms or a trihalomethyl radical such as trichloromethyl or a phenyl radical substituted with a trihalomethyl radical such as trichloromethyl and $R_7$ represents a hydrogen atom, or alternatively $R_6$ and $R_7$, together with the carbon atom to which they are attached, form a 4- to 7-membered ring, replacement of the protective group formed by $R_6$ and $R_7$ by hydrogen atoms may be performed, depending on the meanings of $R_1$, $R_6$ and $R_7$, in the following manner:

a) when $R_1$ represents a tert-butoxycarbonyl radical and $R_6$ and $R_7$, which may be identical or different, represent an alkyl radical or an aralkyl (benzyl) or aryl (phenyl) radical, or alternatively $R_6$ represents a trihalomethyl radical or a phenyl radical substituted with a trihalomethyl radical and $R_7$ represents a hydrogen atom, or alternatively $R_6$ and $R_7$ together form a 4- to 7-membered ring, treatment of the ester of general formula (VI) with an inorganic or organic acid, where appropriate in an organic solvent such as an alcohol, yields the product of general formula:

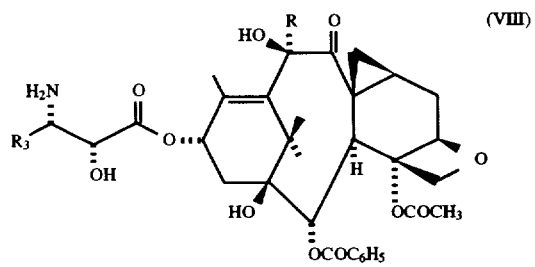

in which R and $R_3$ are defined as above, which is acylated by means of benzoyl chloride in which the phenyl ring is optionally substituted or by means of thenoyl chloride, of furoyl chloride or of a product of general formula:

$R_2$—O—CO—X  (IX)

in which $R_2$ is defined as above and X represents a halogen atom (fluorine, chlorine) or a residue —O—$R_2$ or —O—CO—O—$R_2$, to obtain a product of general formula (I) in which Z represents a radical of general formula (II).

Preferably the product of general formula (VI) is treated with formic acid at a temperature in the region of 20° C.

Preferably, the acylation of the product of general formula (VIII) by means of a benzoyl chloride in which the phenyl radical is optionally substituted or by means of thenoyl chloride, of furoyl chloride or of a product of general formula (IX) is performed in an inert organic solvent chosen from esters such as ethyl acetate, isopropyl acetate or n-butyl acetate and halogenated aliphatic hydrocarbons such as dichloromethane or 1,2-dichloroethane, in the presence of an inorganic base such as sodium bicarbonate or an organic base such as triethylamine. The reaction is performed at a temperature of between 0° and 50° C., and preferably in the region of 20° C.

b) when $R_1$ represents an optionally substituted benzoyl radical, a thenoyl or furoyl radical or a radical $R_2O$—CO— in which $R_2$ is defined as above, $R_6$ represents a hydrogen atom or an alkoxy radical containing 1 to 4 carbon atoms or a phenyl radical substituted with one or more alkoxy radicals containing 1 to 4 carbon atoms and $R_7$ represents a hydrogen atom, replacement of the protective group formed by $R_6$ and $R_7$ by hydrogen atoms is performed in the presence of an inorganic acid (hydrochloric acid, sulphuric acid) or organic acid (acetic acid, methanesulphonic acid, trifluoromethanesulphonic acid, p-toluenesulphonic acid) used alone or mixed in a stoichiometric or catalytic amount, working in an organic solvent chosen from alcohols, ethers, esters, aliphatic hydrocarbons, halogenated aliphatic hydrocarbons and aromatic hydrocarbons at a temperature of between -10° and 60° C., and preferably between 15° and 30° C.

The product of general formula (IV) may be obtained by oxidation of a product of general formula:

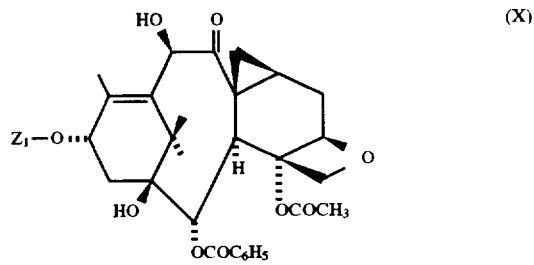

in which $Z_1$ is defined as above.

Generally, the oxidation is carried out by means of an oxidizing agent preferably chosen from pyridinium chlorochromate, pyridinium dichromate, potassium dichromate, ammonium dichromate, pyridinium dichromate or manganese dioxide, under conditions which do not affect the remainder of the molecule.

Depending on the nature of the oxidizing agent used, the oxidation is carried out in an anhydrous organic medium or in an aqueous-organic medium.

Generally, the oxidation is carried out at a temperature of between 0° and 50° C.

The products of general formula (X) may be obtained by the action of an alkali metal halide (sodium chloride, sodium iodide, potassium fluoride) or an alkali metal azide (sodium azide) or a quaternary ammonium salt or an alkali metal phosphate on a baccatin III or 10-deacetylbaccatin III derivative of general formula:

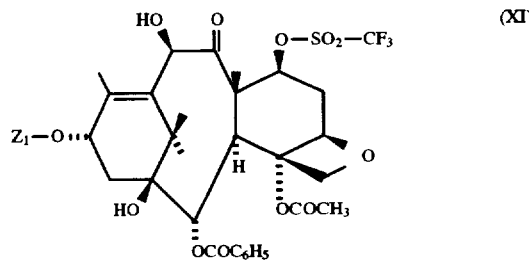

in which $Z_1$ is defined as above.

Generally, the reaction is performed in an organic solvent chosen from ethers (tetrahydrofuran, diisopropyl ether, methyl t-butyl ether) and nitriles (acetonitrile), alone or mixed, at a temperature between 20° C. and the boiling point of the reaction mixture.

The product of general formula (XI) may be obtained by the action by the action of a trifluoromethanesulphonic acid derivative such as the anhydride or N-phenyltrifluoromethanesulphonimide on a product of general formula:

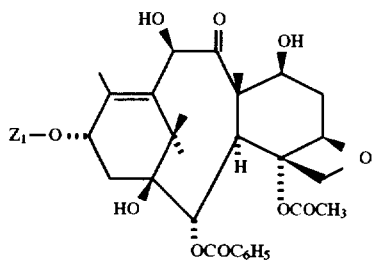

(XII)

in which $Z_1$ is defined as above.

Generally, the reaction is performed in an inert organic solvent (aliphatic hydrocarbons, optionally halogenated, aromatic hydrocarbons) in the presence of an organic base such as a tertiary aliphatic amine (triethylamine) or pyridine at a temperature of between −50° and +20° C.

The products of general formula (XII) may be prepared under the conditions described in European Patents EP 0.253.738 or EP 0.336.841 or in PCT International Application WO 92/09589 the disclosure of which are hereby incorporated by reference.

The new products of general formula (I) obtained by carrying out the processes according to the invention may be purified according to known methods such as crystallization or chromatography.

The products of general formula (I) in which Z represents a radical of general formula (II) display noteworthy biological properties.

In vitro, measurement of the biological activity is performed on tubulin extracted from pig's brain by the method of M. L. Shelanski et al., Proc. Natl. Acad. Sci. USA, 70, 765–768 (1973). Study of the depolymerization of microtubules to tubulin is performed according to the method of G. Chauvière et al., C. R. Acad. Sci., 293, series II, 501–503 (1981). In this study, the products of general formula (I) in which Z represents a radical of general formula (II) was shown to be at least as active as taxol and Taxotere.

In vivo, the products of general formula (I) in which Z represents a radical of general formula (II) were shown to be active in mice grafted with B16 melanoma at doses of between 1 and 10 mg/kg administered intraperitoneally, as well as on other liquid or solid tumours.

The new products have antitumour properties, and more especially activity against tumours which are resistant to Taxol® or to Taxotere®. Such tumours comprise colon tumours which have a high expression of the mdr 1 gene (multiple drug resistance gene). Multiple drug resistance is a customary term relating to the resistance of a tumour to different products having different structures and mechanisms of action. Taxoids are generally known to be strongly recognized by experimental tumours such as P388/DOX, a cell line selected for its resistance to doxorubicin (DOX) which expresses mdr 1.

The examples which follow illustrate the present invention.

EXAMPLE 1

0.116 cm³ of a 3M solution of methylmagnesium iodide in ethyl ether is added dropwise to a solution, maintained under an argon atmosphere at a temperature in the region of −78° C., of 260 mg of 4α-acetoxy-2α- benzoyloxy-5β,20-epoxy-1β-hydroxy-7,8β-methylene-9,10-dioxo-19-nor-11-taxen-13α-yl (2R,4S,5R)-3-tert-butoxycarbonyl-2-(4-methoxyphenyl)-4-phenyl-1,3-oxazolidine-5-carboxylate in 5 cm³ of tetrahydrofuran. After 75 minutes at −78° C., a further 0.116 cm³ of a 3M solution of methylmagnesium iodide in ethyl ether is added dropwise. The reaction mixture is stirred for 30 minutes at −78° C. and then for 18 hours at a temperature in the region of 0° C. After cooling to a temperature in the region of −78° C., 0.116 cm³ of a 3M solution of methylmagnesium iodide in ethyl ether is added dropwise and the mixture is then allowed to react for 20 minutes at −78° C., for 30 minutes at 0° C. and then for 30 minutes at 20° C. The reaction mixture is treated with 1 cm³ of saturated aqueous ammonium chloride solution and 5 cm³ of ethyl acetate. After settling has taken place, the aqueous phase is separated and extracted with 1.5 cm³ of ethyl acetate, and the organic phases are combined, dried over magnesium sulphate, filtered through sintered glass and concentrated under reduced pressure (0.27 kPa) at a temperature in the region of 40° C. 240 mg of an orange-coloured foam are thereby obtained, which product is purified by chromatography at atmospheric pressure on 10 g of silica (0.063–0.2 mm) contained in a column 1.6 cm in diameter (eluent: methanol/dichloromethane, 3:97 by volume), collecting 5 cm³ fractions. Fractions containing only the desired product are pooled and concentrated to dryness under reduced pressure (0.27 kPa) at 40° C. for 2 hours. 0.15 g of 4α-acetoxy-2α-benzoyloxy-5β,20-epoxy-1β,10β-dihydroxy-10α-methyl-7,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate is thereby obtained in the form of a bright yellow foam.

A solution of 75 mg of 4α-acetoxy-2α-benzoyloxy-5β,20-epoxy-1β,10β-dihydroxy-10α-methyl-7,8β-methylene-9-oxo-19-nor-11-taxen-13α-yl (2R,4S,4R)-3-tert-butoxycarbonyl-2-(4-methoxyphenyl)-4-phenyl-1,3-oxazolidine-5-carboxylate in 1.5 cm³ of a 0.1N solution of hydrochloric acid in ethanol is stirred at a temperature in the region of 20° C. for 5 hours. A further 0.5 cm³ of 0.1N hydrochloric acid in ethanol is added. After 16 hours at a temperature in the region of 5° C., a further 0.5 cm³ of 0.1N hydrochloric acid in ethanol is added and the solution is stirred for a further 3 hours at a temperature in the region of 20° C. The reaction mixture is diluted with 2.5 cm³ of dichloromethane, 2.5 cm³ of saturated aqueous sodium hydrogen carbonate solution and 2 cm³ of distilled water. After settling has taken place, the aqueous phase is separated and extracted with 5 cm³ of dichloromethane, and the organic phases are combined, dried over magnesium sulphate, filtered through sintered glass and concentrated under reduced pressure (0.27 kPa) at a temperature in the region of 40° C. 124 mg of a yellow foam are thereby obtained, which product is purified by preparative thin-layer chromatography [5 Merck preparative plates, Silica gel 60F$_{254}$, thickness 0.5 mm, application in solution in dichloromethane, eluent: methanol/dichloromethane (5:95 by volume) mixture]. After elution of the zone corresponding to the major product with a methanol/dichloromethane (10:90 by volume) mixture, filtration through sintered glass and then evaporation of the solvents under reduced pressure (0.27 kPa) at a temperature in the region of 40° C., 37 mg of 4α-acetoxy-2α-benzoyloxy-5β,20-epoxy-1β,10β-dihydroxy-10α-methyl-7,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

¹H NMR spectrum (600 MHz, CDCl$_3$, δ in ppm): 1.21 (s, 3H:CH$_3$); 1.22 (s, 9H:C(CH$_3$)$_3$); 1.28 (s, 3H:CH$_3$); 1.38 (mt, 1H:H at position 7); 1.68 and 2.31 (2 mt, 1H each:CH$_2$ at position 19); 1.70 (s, 3H:CH$_3$ at position 10); 1.85 (s, 1H:OH at position 1); 1.87 (s, 3H:CH$_3$); 2.17 and 2.33 (2 mt, 1H each:CH$_2$ at position 14); 2.17 and 2.43 (respectively d and dt, J=16 and J=16 and 4.5 Hz, 1H each:CH$_2$ at position 6); 2.41 (s, 3H:COCH$_3$); 3.25 (mt, 1H:OH at position 2'); 4.05 and 4.35 (2d, J=9 Hz, 1H each:CH$_2$ at position 20); 4.30 (d, J=7 Hz, 1H:H at position 3); 4.42 (s, 1H:OH at position 10); 4.60 (mt, 1H:H at position 2'); 4.75 (d, J=4 Hz, 1H:H at position 5); 5.30 (mt, 1H:H at position 3'); 5.38 (d, J=10 Hz, 1H:CONH); 5.67 (d, J=7 Hz, 1H:H at position 2); 6.33 (broad t, J=9 Hz, 1H:H at position 13); 7.30 (t, J=7.5 Hz, 1H:aromatic at position 3' H at para position); 7.37 (d, J=7.5 Hz, 2H:aromatic at position 3' H at ortho position); 7.40 (t, J=7.5 Hz, 2H:aromatic at position 3' H at meta position); 7.51 (t, J=7.5 Hz, 2H:OCOC$_6$H$_5$ H at meta position); 7.60 (t, J=7.5 Hz, 1H:OCOC$_6$H$_5$ H at para position); 8.17 (d, J=7.5 Hz, 2H:OCOC$_6$H$_5$ H at ortho position).

4α-Acetoxy-2α-benzoyloxy-5β,20-epoxy-1β,-hydroxy-7,8β-methylene-9,10-dioxo-19-nor-11-taxen-13α-yl (2R, 4S,5R)-3-tert-butoxycarbonyl-2-(4-methoxyphenyl)-4-phenyl-1,3-oxazolidine-5-carboxylate may be prepared in the following manner:

0.5 g of 4 Å molecular sieve is added to a solution, maintained under an argon atmosphere at a temperature in the region of 20° C., of 900 mg of 4α-acetoxy-2α-benzoyloxy-5β,20-epoxy-1β,10β-dihydroxy-7,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate in 9 cm$^3$ of dichloromethane, and 0.43 g of pyridinium chlorochromate is then added portionwise under the same conditions. The reaction mixture is stirred for 90 minutes at a temperature in the region of 20° C. and then filtered through sintered glass lined with Clarcel. After the solid residue is rinsed with dichloromethane, the filtrates are concentrated under reduced pressure (0.27 kPa) at a temperature in the region of 40° C. 1.13 g of a brown resin are thereby obtained, which product is purified by chromatography at atmospheric pressure on 40 g of silica (0.063–0.2 mm) contained in a column 2.2 cm in diameter (eluent: methanol/dichloromethane, 2:98 by volume), collecting 10 cm$^3$ fractions. Fractions containing only the desired product are pooled and concentrated to dryness under reduced pressure (0.27 kPa) at 40° C. for 2 hours. 0.63 g of 4α-acetoxy-2α-benzoyloxy-5β,20-epoxy-1β-hydroxy-7,8β-methylene-9,10-dioxo-19-nor-11-taxen-13α-yl (2R, 4S,5R)-3-tert-butoxycarbonyl-2-(4-methoxyphenyl)-4-phenyl-1,3-oxazolidine-5-carboxylate is thereby obtained in the form of a yellow-green foam.

4α-Acetoxy-2αbenzoyloxy-5β,20-epoxy-1β,10-dihydroxy-7,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

1.5 g of sodium chloride and 0.5 g of 4 Å molecular sieve is added to a solution of 1.8 g 4α-acetoxy-2α-benzoyloxy-5β,20-epoxy-1β,10β-dihydroxy-9-oxo-7β-trifluoromethanesulphonyloxy-11-taxen-13α-yl (2R,4S,5R)-3-tert-butoxycarbonyl-2-(4-methoxyphenyl)-4-phenyl-1,3-oxazolidine-5-carboxylate in 20 cm$^3$ of acetonitrile and 3 cm$^3$ of tetrahydrofuran. The reaction mixture is brought to reflux under an inert argon atmosphere for 1 hour, brought back to a temperature in the region of 20° C. and filtered through sintered glass. The solid residue is rinsed with 10 cm$^3$ of ethyl acetate. The filtrates are combined, dried over magnesium sulphate, filtered through sintered glass and concentrated under reduced pressure (0.27 kPa) at a temperature in the region of 40° C. 1.6 g of a yellow foam are thereby obtained, which product is purified by chromatography at atmospheric pressure on 60 g of silica (0.063–0.2 mm) contained in a column 3 cm in diameter (eluent: ethyl acetate/dichloromethane, 20:80 by volume), collecting 10 cm$^3$ fractions. Fractions containing only the desired product are pooled and concentrated to dryness under reduced pressure (0.27 kPa) at 40° C. for 2 hours. 0.91 g of 4α-acetoxy-2α-benzoyloxy-5β,20-epoxy-1β,10β-dihydroxy-7,8β-methylene-9-oxo-19-nor-11-taxen-13α-yl (2R,4S,5R)-3-tert-butoxycarbonyl-2-(4-methoxyphenyl)-4-phenyl-1,3-oxazolidine-5-carboxylate is thereby obtained in the form of a white foam.

4α-Acetoxy-2α-benzoyloxy-5β,20-epoxy-1β,10β-dihydroxy-9-oxo-7β-trifluoromethanesulphonate-11-taxen-13α-yl (2R,4S,5R)-3-tert-butoxycarbonyl-2-(4-methoxyphenyl)-4-phenyl-1,3-oxazolidine-5-carboxylate may be prepared in the following manner:

0.54 cm$^3$ of trifluoromethanesulphonic anhydride is added dropwise to a solution, maintained under an argon atmosphere at a temperature in the region of −35° C., of 1.9 g of 4α-acetoxy-2α-benzoyloxy-5β,20-epoxy-1β,7β,10β-trihydroxy-9-oxo-11-taxen-13α-yl (2R,4S,5R)-3-tert-butoxycarbonyl-2-(4-methoxyphenyl)-4-phenyl-1,3-oxazolidine-5-carboxylate in 20 cm$^3$ of anhydrous dichloromethane and 0.68 cm$^3$ of anhydrous pyridine. The reaction mixture is stirred for 10 minutes at −35° C. and 90 minutes at a temperature in the region of −5° C., and 5 cm$^3$ of distilled water are then added to it at a temperature in the region of −15° C. After settling has taken place, the aqueous phase is separated and re-extracted with 2 cm$^3$ of dichloromethane, and the organic phases are combined, dried over magnesium sulphate, filtered through sintered glass and concentrated under reduced pressure (0.27 kPa) at a temperature in the region of 40° C. 2.4 g of a yellow oil are thereby obtained, which product is purified by chromatography at atmospheric pressure on 100 g of silica (0.063–0.2 mm) contained in a column 3.2 cm in diameter (eluent: methanol/dichloromethane, 2:98 by volume), collecting 15 cm$^3$ fractions. Fractions containing only the desired product are pooled and concentrated to dryness under reduced pressure (0.27 kPa) at 40° C. for 2 hours. 1.23 g of 4α-acetoxy-2α-benzoyloxy-5β,20-epoxy-1β,10-dihydroxy-9-oxo-7-trifluoromethanesulphonate-11-taxen-13α-yl (2R,4S,5R)-3-tert-butoxycarbonyl-2-(4-methoxyphenyl)-4-phenyl-1,3-oxazolidine-5-carboxylate are thereby obtained in the form of a pale yellow foam.

4α-Acetoxy-2α-benzoyloxy-5β,20-epoxy-1,7β,10β-trihydroxy-9-oxo-11-taxen-13α-yl (2R,4S,5R))-3-tert-butoxycarbonyl-2-(4-methoxyphenyl)-4-phenyl-1,3-oxazolidine-5-carboxylate may be prepared in the following manner:

A solution of 3.95 g of 4-acetoxy-2α-benzoyloxy-5β,20-epoxy-1β-hydroxy-9-oxo-7β,10β-bis(2,2,2-trichloroethoxy)carbonyloxy-11-taxen-13α-yl (2R,4S,5R)-3-tert-butoxycarbonyl-2-(4-methoxyphenyl)-4-phenyl-1,3-oxazolidine-5-carboxylate in a mixture of 20 cm$^3$ of methanol and 7 cm$^3$ of acetic acid is heated with stirring under an argon atmosphere to a temperature in the region of 60° C., and 2 g of powdered zinc are then added to it. The reaction mixture is then stirred for 15 minutes at 60° C., thereafter cooled to a temperature in the region of 20° C. and filtered through sintered glass lined with Celite. The sintered glass is washed with 2 times 15 cm$^3$ of methanol. The filtrate is concentrated to dryness under reduced pressure (0.27 kPa) at a temperature in the region of 40° C. 100 cm$^3$ of dichloromethane are added to the residue. The organic phase is washed with 2 times 10 cm$^3$ of saturated aqueous sodium hydrogen carbonate solution and then with 10 cm$^3$ of distilled water. The organic phase is dried over magnesium sulphate, filtered through sintered glass and then concentrated to dryness under reduced pressure (2.7 kPa) at 40° C. 5.57 g of a white foam are obtained, which product is purified by chromatography on 300 g of silica (0.063–0.2 mm) contained in a column 6 cm in diameter (elution gradient: methanol/dichloromethane, from 0:100 to 2:98 by volume), collecting 100 cm$^3$ fractions. Fractions containing only the desired product are pooled and concentrated to dryness under reduced pressure (0.27 kPa) at 40° C. for 2 hours. 2.52 g of 4-acetoxy-2α-benzoyloxy-5β,20-epoxy-1, 7β,10β-trihydroxy-9-oxo-11-taxen-13α-yl (2R,4S,5R))-3-tert-butoxycarbonyl-2-(4-methoxyphenyl)-4-phenyl-5-oxazolidinecarboxylate are thereby obtained in the form of a white foam.

4-Acetoxy-2α-benzoyloxy-5β,20-epoxy-1β-hydroxy-9-oxo-7β,10β-bis(2,2,2-trichloroethoxy)carbonyloxy-11-taxen-13α-yl (2R,4S,5R))-3-tert-butoxycarbonyl-2-(4-methoxyphenyl)-4-phenyl-1,3-oxazolidine-5-carboxylate may be prepared under the conditions described in PCT International Application WO 94/07878 the disclosure of which is incorporated by reference.

The new products of general formula (I) in which Z represents a radical of general formula (II) manifest significant inhibitory activity with respect to abnormal cell proliferation, and possess therapeutic properties permitting the treatment of patients having pathological conditions associated with abnormal cell proliferation. The pathological conditions include the abnormal cell proliferation of malignant or non-malignant cells of various tissues and/or organs, comprising, without implied limitation, muscle, bone or connective tissue, the skin, brain, lungs, sex organs, the lymphatic or renal systems, mammary or blood cells, liver, the digestive system, pancreas and thyroid or adrenal glands. These pathological conditions can also include psoriasis, solid tumours, cancers of the ovary, breast, brain, prostate, colon, stomach, kidney or testicles, Kaposi's sarcoma, cholangiocarcinoma, choriocarcinoma, neuroblastoma, Wilms' tumour, Hodgkin's disease, melanoma, multiple myeloma, chronic lymphocytic leukaemia and acute or chronic granulocytic lymphoma. The new products according to the invention are especially useful for the treatment of cancer of the ovary. The products according to the invention may be used to prevent or delay the appearance or reappearance of the pathological conditions, or to treat these pathological conditions.

The products according to the invention may be administered to a patient according to different dosage forms suited to the chosen administration route, which is preferably the parenteral route. Parenteral administration comprises intravenous, intraperitoneal, intramuscular or subcutaneous administration. Intraperitoneal or intravenous administration is more especially preferred.

The present invention also comprises pharmaceutical compositions containing at least one product of general formula (I), in a sufficient amount suitable for use in human or veterinary therapy. The compositions may be prepared according to the customary methods, using one or more pharmaceutically acceptable adjuvants, vehicles or excipients. Suitable vehicles include diluents, sterile aqueous media and various non-toxic solvents. Preferably, the compositions take the form of aqueous solutions or suspensions, injectable solutions which can contain emulsifying agents, colourings, preservatives or stabilizers.

The choice of adjuvants or excipients may be determined by the solubility and chemical properties of the product, the particular mode of administration and good pharmaceutical practice.

For parenteral administration, sterile, aqueous or non-aqueous solutions or suspensions are used. For the preparation of non-aqueous solutions or suspensions, natural vegetable oils such as olive oil, sesame oil or liquid petroleum, or injectable organic esters such as ethyl oleate, may be used. The sterile aqueous solutions can consist of a solution of a pharmaceutically acceptable salt dissolved in water. The aqueous solutions are suitable for intravenous administration provided the pH is appropriately adjusted and the solution is made isotonic, for example with a sufficient amount of sodium chloride or glucose. The sterilization may be carried out by heating or by any other means which does not adversely affect the composition.

It is clearly understood that all the products participating in the compositions according to the invention must be pure and non-toxic in the amounts used.

The compositions can contain at least 0.01% of therapeutically active product. The amount of active product in a composition is such that a suitable dosage can be prescribed. Preferably, the compositions are prepared in such a way that a single dose contains from 0.01 to 1000 mg approximately of active product for parenteral administration.

The therapeutic treatment may be performed concurrently with other therapeutic treatments including antineoplastic drugs, monoclonal antibodies, immunotherapy or radiotherapy or biological response modifiers. The response modifiers include, without implied limitation, lymphokines and cytokines such as interleukins, interferons (α, β or δ) and TNF. Other chemotherapeutic agents which are useful in the treatment of disorders due to abnormal cell proliferation include, without implied limitation, alkylating agents, for instance nitrogen mustards such as mechloretamine, cyclophosphamide, melphalan and chlorambucil, alkyl sulphonates such as busulfan, nitrosoureas such as carmustine, lomustine, semustine and streptozocin, triazenes such as dacarbazine, antimetabolites such as folic acid analogues, for instance methotrexate, pyrimidine analogues such as fluorouracil and cytarabine, purine analogues such as mercaptopurine and thioguanine, natural products, for instance vinca alkaloids such as vinblastine, vincristine and vendesine, epipodophyllotoxins such as etoposide and teniposide, antibiotics such as dactinomycin, daunorubicin, doxorubicin, bleomycin, plicamycin and mitomycin, enzymes such as L-asparaginase, various agents such as coordination complexes of platinum, for instance cisplatin, substituted ureas such as hydroxyurea, methylhydrazine derivatives such as procarbazine, adrenocortical suppressants such as mitotane and aminoglutethimide, hormones and antagonists such as adrenocorticosteroids such as prednisone, progestins such as hydroxyprogesterone caproate, methoxyprogesterone acetate and megestrol acetate, oestrogens such as diethylstilboestrol and ethynyloestradiol, antioestrogens such as tamoxifen, and androgens such as testosterone propionate and fluoxymesterone.

The doses used for carrying out the methods according to the invention are those which permit a prophylatic treatment or a maximum therapeutic response. The doses vary according to the administration form, the particular product selected and features distinctive to the subject to be treated. In general, the doses are those which are therapeutically effective for the treatment of disorders due to abnormal cell proliferation. The products according to the invention may be administered as often as necessary to obtain the desired therapeutic effect. Some patients may respond rapidly to relatively high or low doses, and then require low or zero maintenance doses. Generally, low doses will be used at the beginning of the treatment and, if necessary, increasingly stronger doses will be administered until an optimum effect is obtained. For other patients, it may be necessary to administer maintenance doses 1 to 8 times a day, and preferably 1 to 4 times, according to the physiological requirements of the patient in question. It is also possible that some patients may require the use of only one to two daily administrations.

In man, the doses are generally between 0.01 and 200 mg/kg. For intraperitoneal administration, the doses will generally be between 0.1 and 100 mg/kg, preferably between 0.5 and 50 mg/kg and still more specifically between 1 and 10 mg/kg. For intravenous administration, the doses are generally between 0.1 and 50 mg/kg, preferably between 0.1 and 5 mg/kg and still more specifically between 1 and 2 mg/kg. It is understood that, in order to choose the most suitable dosage, account should be taken of the administration route, the patient's weight, general state of health and age and all factors which may influence the efficacy of the treatment.

The example which follows illustrates a composition according to the invention.

EXAMPLE 40 mg of the product obtained in Example 1 are dissolved in 1 cm$^3$ of Emulphor EL 620 and 1 cm$^3$ of ethanol, and the solution is then diluted by adding 18 cm$^3$ of physiological saline.

The composition is administered by perfusion over 1 hour by introduction in physiological solution.

We claim:

1. A taxoid of the formula (I):

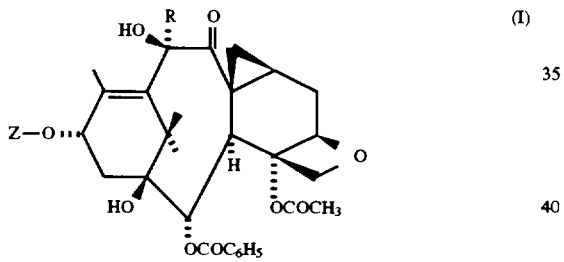

wherein:

R represents an unbranched or branched alkyl radical comprising 1 to 6 carbon atoms, an unbranched or branched alkenyl radical comprising 2 to 6 carbon atoms, an unbranched or branched alkynyl radical comprising 2 to 6 carbon atoms, a cycloalkyl radical comprising 3 to 6 carbon atoms, a cycloalkenyl radical comprising 4 to 6 carbon atoms, an aryl radical, or a 5- to 6-membered aromatic heterocyclic radical;

Z represents a hydrogen atom or a radical of the formula (II):

wherein:

$R_1$ represents a benzoyl radical unsubstituted or substituted with at least one substituent selected from a halogen atom, an alkyl radical comprising 1 to 4 carbon atoms, an alkoxy radical comprising 1 to 4 carbon atoms, a trifluoromethyl radical, a thenoyl radical, a furoyl radical, or a radical $R_2$—O—CO— in which $R_2$ represents:

an alkyl radical comprising 1 to 8 carbon atoms, an alkenyl radical comprising 2 to 8 carbon atoms, an alkynyl radical comprising 3 to 8 carbon atoms, a cycloalkyl radical comprising 3 to 6 carbon atoms, a cycloalkenyl radical comprising 4 to 6 carbon atoms, or a bicycloalkyl radical comprising 7 to 10 carbon atoms, these radicals being unsubstituted or substituted with at least one substituent selected from the group consisting of a halogen atom, a hydroxyl radical, an alkoxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted at the 4 position with an alkyl radical comprising 1 to 4 carbon atoms or with a phenylalkyl radical in which the alkyl portion comprises 1 to 4 carbon atoms), a cycloalkyl radical comprising 3 to 6 carbon atoms, a cycloalkenyl radical comprising 4 to 6 carbon atoms, a phenyl radical (unsubstituted or substituted with at least one substituent selected from the group consisting of a halogen atom, an alkyl radical comprising 1 to 4 carbon atoms, and an alkoxy radical comprising 1 to 4 carbon atoms), a cyano radical, a carboxyl radical, and an alkoxycarbonyl radical in which the alkyl portion comprises 1 to 4 carbon atoms;

a phenyl or α- or β-naphthyl radical unsubstituted or substituted with at least one substituent selected from the group consisting of a halogen atom, an alkyl radical comprising 1 to 4 carbon atoms, an alkoxy radical comprising 1 to 4 carbon atoms, and a 5-membered aromatic heterocyclic radical; or a saturated heterocyclic radical comprising 4 to 6 carbon atoms, unsubstituted or substituted with at least one alkyl radical comprising 1 to 4 carbon atoms;

$R_3$ represents an unbranched or branched alkyl radical comprising 1 to 8 carbon atoms, an unbranched or branched alkenyl radical comprising 2 to 8 carbon atoms, an unbranched or branched alkynyl radical comprising 2 to 8 carbon atoms, a cycloalkyl radical comprising 3 to 6 carbon atoms, a phenyl or α- or β-naphthyl radical unsubstituted or substituted with at least one substituent selected from the group consisting of a halogen atom and an alkyl, alkenyl, alkynyl, aryl, aralkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, alkylcarbamoyl, dialkylcarbamoyl, cyano, nitro, and trifluoromethyl radical, or a 5-membered aromatic heterocycle comprising at least one heteroatom, identical or different, selected from nitrogen, oxygen or sulphur atoms and unsubstituted or substituted with at least one substituent, identical or different, selected from the group consisting of a halogen atom and an alkyl, aryl, amino, alkylamino, dialkylamino, alkoxycarbonylamino, acyl, arylcarbonyl, cyano, carboxyl, carbamoyl, alkylcarbamoyl, dialkylcarbamoyl, and alkoxycarbonyl radical, wherein for the substituents of the phenyl, α- or β-naphthyl and aromatic heteroeocyclic radicals, the alkyl radicals and alkyl portions of the other radicals comprise 1 to 4 carbon atoms, the alkenyl and alkynyl radicals comprise 2 to 8 carbon atoms, and the aryl radicals are phenyl or α- or β-naphthyl radicals.

2. The taxoid according to claim 1 wherein

R represents an alkyl radical comprising 1 to 4 carbon atoms;

Z represents a hydrogen atom or a radical of the formula (II) in which $R_1$ represents a benzoyl radical or a radical $R_2$—O—CO— in which $R_2$ represents a tert-butyl radical; and $R_3$ represents an alkyl radical comprising 1 to 6 carbon atoms, an alkenyl radical comprising 2 to 6 carbon atoms, a cycloalkyl radical comprising 3 to 6 carbon atoms, a phenyl radical unsubstituted or substituted with at least one, identical or different, substituent selected from the group consisting of a halogen atom and an alkyl, alkoxy, dialkylamino, acylamino, alkoxycarbonylamino, trifluoromethyl, 2- or 3-furyl, 2- or 3-thienyl, and 2-, 4- or 5-thiazolyl radical.

3. The taxoid according to claim 1 wherein

R represents a methyl radical;

Z represents a hydrogen atom or a radical of the formula (II) in which $R_1$, represents a benzoyl radical or a radical $R_2$—O—CO— in which $R_2$ represents a tert-butyl radical; and $R_3$ represents an isobutyl, isobutenyl, butenyl, cyclohexyl, phenyl, 2-furyl, 3-furyl, 2-thienyl, 3-thienyl, 2-thiazolyl, 4-thiazolyl, or 5-thiazolyl radical.

4. A process for preparing a taxoid according to claim 1 wherein an organometallic derivative of the formula (III):

R—X$_1$            (III)

wherein R is defined as in claim 1 and $X_1$ represents a metal atom or an organomagnesium residue;

is reacted with a compound of the formula (IV):

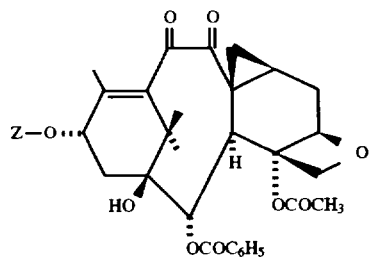

(IV)

wherein $Z_1$ represents a hydrogen atom or a radical of the formula (V):

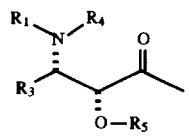

(V)

wherein $R_1$ and $R_3$ are defined as in claim 1, and either $R_4$ represents a hydrogen atom and $R_5$ represents a group protecting the hydroxyl function or $R_4$ and $R_5$ together form a heterocycle;

to obtain a product of the formula (VI):

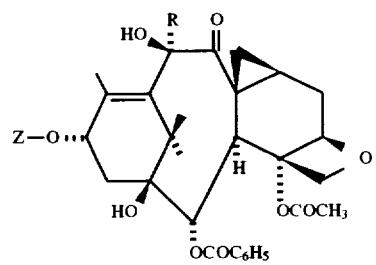

(VI)

wherein $Z_1$ and R are defined as in claim 1;

and the protective groups represented by $R_5$ or $R_4$ and $R_5$ are, where appropriate, replaced by hydrogen atoms.

5. The process according to claim 4, wherein the organometallic derivative is reacted by working in an inert organic solvent at a temperature of about −78° to about +30° C.

6. The process according to claim 4, wherein when $R_4$ represents a hydrogen atom and $R_5$ represents a group protecting the hydroxyl function, comprising replacing the $R_5$ protecting group with a hydrogen atom by using an inorganic or organic acid, or combination thereof, working in an organic solvent selected from alcohols, ethers, esters, aliphatic hydrocarbons, halogenated aliphatic hydrocarbons, aromatic hydrocarbons, or nitriles at a temperature of about −10° to about 60° C.

7. The process according to claim 4, wherein when $R_4$ and $R_5$ together form an oxazolidine ring of the formula (VII):

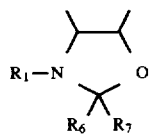

(VII)

wherein $R_1$ is defined as in claim 1; and $R_6$ and $R_7$, which may be identical or different, represent a hydrogen atom or an alkyl radical comprising 1 to 4 carbon atoms, an aralkyl radical in which the alkyl portion comprises 1 to 4 carbon atoms, an aryl radical; or alternatively $R_6$ represents an alkoxy radical comprising 1 to 4 carbon atoms, a trihalomethyl radical, or a phenyl radical substituted with a trihalomethyl radical, and $R_7$ represents a hydrogen atom; or alternatively $R_6$ and $R_7$, together with the carbon atom to which they are attached, form a 4- to 7-membered ring;

comprising replacing the protecting groups formed by $R_6$ and $R_7$ with hydrogen, depending on the meanings of $R_1$, $R_6$ and $R_7$, in the following manner:

a) when $R_1$ represents a tert-butoxycarbonyl radical and $R_6$ and $R_7$, which may be identical or different, represent an alkyl radical, an aralkyl radical, or an aryl radical; or alternatively R6 represents a trihalomethyl radical or a phenyl radical substituted with a trihalomethyl radical and $R_7$ represents a hydrogen atom; or alternatively R6 and $R_7$ together form a 4- to 7-membered ring; the protecting groups are replaced by treating the ester of formula (VI) with an inorganic or organic acid, where appropriate in an organic solvent selected from an alcohol, to yield the product of the formula (VIII):

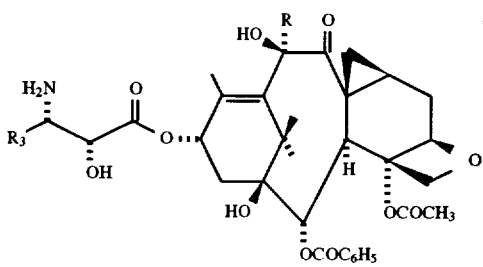

(VIII)

wherein R and $R_3$ are defined as in claim 1; and the product of formula (VII) is acylated by using benzoyl chloride in which the phenyl ring is unsubstituted or substituted by thenoyl chloride, furoyl chloride, or a compound of formula (IX):

$R_2$—O—CO—$X_2$   (IX)

wherein $R_2$ is defined as in claim 1 and $X_2$ represents a halogen atom or a residue —O—$R_2$ or —O—CO—O—$R_2$; to obtain a product of the formula (I) in which Z represents a radical of the formula (II);

b) when $R_1$ represents an unsubstituted or substituted benzoyl radical, a thenoyl radical, furoyl radical, or a radical $R_2$O—CO— in which $R_2$ is defined as in claim 1; $R_6$ represents a hydrogen atom, an alkoxy radical comprising 1 to 4 carbon atoms, or a phenyl radical substituted with at least one alkoxy radical comprising 1 to 4 carbon atoms and $R_7$ represents a hydrogen atom; the protecting group formed by $R_6$ and $R_7$ is replaced by a hydrogen atom in the presence of an inorganic or organic acid or combination thereof in a stoichiometric or catalytic amount, working in an organic solvent selected from alcohols, ethers, esters, aliphatic hydrocarbons, halogenated aliphatic hydrocarbons and aromatic hydrocarbons at a temperature of about $-10°$ to about $60°$ C.

8. A pharmaceutical composition comprising at least one taxoid according to claim 1 in which Z represents a radical of the formula (II) and at least one pharmaceutically acceptable product.

9. The taxoid according to claim 1, wherein the $R_2$ 5-membered aromatic heterocyclic radical is a furyl or thienyl radical.

10. The taxoid according to claim 2, wherein the halogen atom substituent for the $R_2$ phyenyl radical is fluorine or chlorine.

11. The taxoid according to claim 4, wherein $X_1$ represents a lithium atom.

12. The taxoid according to claim 7, wherein the aryl portion of the $R_6$ or $R_7$ aralkyl radical is a phenyl radical unsubstituted or substituted with at least one alkoxy radical comprising 1 to 4 carbon atoms.

13. The taxoid according to claim 7, wherein the $R_6$ or $R_7$ aryl radical is a phenyl radical unsubstituted or substituted with at least one alkoxy radical comprising 1 to 4 carbon atoms.

14. The taxoid according to claim 7, wherein the trihalomethyl radical is a trichloromethyl radical.

15. The taxoid according to claim 7, wherein the halogen atom of $X_2$ is fluorine or chlorine.

16. A pharmaceutical composition comprising a taxoid according to claim 1 in which Z represents a formula (II) radical and a pharmaceutically acceptable carrier.

* * * * *

UNITED STATES PATENT AND TRADEMARK OFFICE
CERTIFICATE OF CORRECTION

PATENT NO. : 5,777,139
DATED : July 7, 1998
INVENTOR(S) : Hervé Bouchard et al.

It is certified that error appears in the above-identified patent and that said Letters Patent is hereby corrected as shown below:

On the Title Page, Item [57], Inventors, change "Boureat" to --Bourzat--;

Claim 3, Column 15, Line 22, after "$R_1$" delete --,--;

Claim 6, Column 16, Line 29, change "nitrites" to --nitriles--;

Claim 7, Column 16, Line 59, change "R6" to --$R_6$--;

Claim 7, Column 16, Line 62, change "R6" to --$R_6$--.

Signed and Sealed this

Seventeenth Day of August, 1999

Attest:

Q. TODD DICKINSON

*Attesting Officer*     Acting Commissioner of Patents and Trademarks